United States Patent
Williams

(10) Patent No.: US 10,653,414 B2
(45) Date of Patent: May 19, 2020

(54) ANVIL ASSEMBLY WITH SLIDING SLEEVE

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 345 days.

(21) Appl. No.: 15/609,062

(22) Filed: May 31, 2017

(65) Prior Publication Data

US 2017/0265857 A1  Sep. 21, 2017

Related U.S. Application Data

(63) Continuation of application No. 14/023,694, filed on Sep. 11, 2013, now Pat. No. 9,693,773.

(51) Int. Cl.
*A61B 17/068*  (2006.01)
*A61B 17/11*  (2006.01)
*A61B 17/115*  (2006.01)
*A61B 17/00*  (2006.01)

(52) U.S. Cl.
CPC .......... *A61B 17/068* (2013.01); *A61B 17/115* (2013.01); *A61B 17/1114* (2013.01); *A61B 17/1155* (2013.01); *A61B 2017/00473* (2013.01)

(58) Field of Classification Search
CPC . A61B 17/068; A61B 17/1114; A61B 17/115; A61B 17/1155; A61B 2017/00473
USPC .............................. 606/218; 227/175.1–182.1
See application file for complete search history.

(56) References Cited

U.S. PATENT DOCUMENTS

| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |

(Continued)

FOREIGN PATENT DOCUMENTS

| CA | 908529 A | 8/1972 |
| DE | 1057729 B | 5/1959 |

(Continued)

OTHER PUBLICATIONS

European Examination Report dated Sep. 27, 2917, issued in EP Application No. 16174842.

(Continued)

*Primary Examiner* — Robert F Long
*Assistant Examiner* — Xavier A Madison
(74) *Attorney, Agent, or Firm* — Carter, DeLuca & Farrell LLP

(57) ABSTRACT

An anvil assembly is provided. The anvil assembly includes an anvil center rod, a head assembly pivotally secured to the anvil center rod assembly from an operative position to a tilted position, and a sleeve slidably disposed about the anvil center rod. The sleeve is associated with the head assembly such that movement of the head assembly from the operative position towards the tilted position effects proximal movement of the sleeve about the anvil center rod.

18 Claims, 12 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |

(56) References Cited

U.S. PATENT DOCUMENTS

| | | |
|---|---|---|
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 * | 10/2005 | Aranyi ............... A61B 17/072 227/176.1 |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |

(56) References Cited

U.S. PATENT DOCUMENTS

| | | | |
|---|---|---|---|
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marozyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,109,426 B2 | 2/2012 | Milliman et al. | |
| 9,010,605 B2 * | 4/2015 | Olson | A61B 17/1155 227/175.1 |
| 9,016,547 B2 | 4/2015 | Mozdzierz et al. | |
| 9,693,773 B2 | 7/2017 | Williams | |
| 2003/0111507 A1 | 6/2003 | Nunez | |
| 2005/0023325 A1 | 2/2005 | Gresham et al. | |
| 2005/0051597 A1 | 3/2005 | Toledano | |
| 2005/0107813 A1 | 5/2005 | Gilete Garcia | |
| 2005/0125009 A1 | 6/2005 | Perry et al. | |
| 2005/0145674 A1 | 7/2005 | Sonnenschein et al. | |
| 2005/0145675 A1 | 7/2005 | Hartwick et al. | |
| 2006/0000869 A1 | 1/2006 | Fontayne | |
| 2006/0011698 A1 | 1/2006 | Okada et al. | |
| 2006/0047307 A1 | 3/2006 | Ortiz et al. | |
| 2006/0144897 A1 | 7/2006 | Jankowski et al. | |
| 2006/0201989 A1 | 9/2006 | Ojeda | |
| 2006/0241692 A1 | 10/2006 | McGuckin et al. | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2007/0257082 A1 | 11/2007 | Milliman | |
| 2008/0230581 A1 | 9/2008 | Marczyk et al. | |
| 2009/0230170 A1 | 9/2009 | Milliman | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0255976 A1 | 10/2009 | Marczyk et al. | |
| 2009/0302089 A1 | 12/2009 | Harari et al. | |
| 2010/0001037 A1 | 1/2010 | Racenet et al. | |
| 2010/0019016 A1 | 1/2010 | Edoga et al. | |
| 2010/0038401 A1 | 2/2010 | Milliman et al. | |
| 2010/0051668 A1 | 3/2010 | Milliman et al. | |
| 2010/0065607 A1 | 3/2010 | Orban, III et al. | |
| 2010/0084453 A1 | 4/2010 | Hu | |
| 2010/0089971 A1 | 4/2010 | Milliman et al. | |
| 2010/0108739 A1 | 5/2010 | Holsten et al. | |
| 2010/0108740 A1 | 5/2010 | Pastorelli et al. | |
| 2010/0108741 A1 | 5/2010 | Hessler et al. | |
| 2010/0133319 A1 | 6/2010 | Milliman et al. | |
| 2010/0147923 A1 | 6/2010 | D'Agostino et al. | |
| 2010/0163598 A1 | 7/2010 | Belzer | |
| 2010/0170932 A1 | 7/2010 | Wenchell et al. | |
| 2010/0224668 A1 | 9/2010 | Fontayne et al. | |
| 2010/0230465 A1 | 9/2010 | Smith et al. | |
| 2010/0230466 A1 | 9/2010 | Criscuolo et al. | |
| 2010/0230467 A1 | 9/2010 | Criscuolo et al. | |
| 2010/0258611 A1 | 10/2010 | Smith et al. | |
| 2010/0264195 A1 | 10/2010 | Bettuchi | |
| 2010/0270356 A1 | 10/2010 | Holsten et al. | |
| 2010/0282815 A1 | 11/2010 | Bettuchi et al. | |
| 2010/0301098 A1 | 12/2010 | Kostrzewski | |
| 2010/0327041 A1 | 12/2010 | Milliman et al. | |
| 2011/0006100 A1 | 1/2011 | Milliam | |
| 2011/0006102 A1 | 1/2011 | Kostrzewski | |
| 2011/0011916 A1 | 1/2011 | Levine | |
| 2011/0017800 A1 | 1/2011 | Viola | |
| 2011/0024476 A1 | 2/2011 | Bettuchi et al. | |
| 2011/0024481 A1 | 2/2011 | Bettuchi et al. | |
| 2011/0036889 A1 | 2/2011 | Heinrich et al. | |
| 2011/0036894 A1 | 2/2011 | Bettuchi | |
| 2011/0042442 A1 | 2/2011 | Viola et al. | |
| 2011/0042443 A1 | 2/2011 | Milliman et al. | |
| 2011/0057016 A1 | 3/2011 | Bettuchi | |
| 2011/0089219 A1 | 4/2011 | Hessler | |
| 2011/0095067 A1 | 4/2011 | Ohdaira | |
| 2011/0095068 A1 | 4/2011 | Patel | |
| 2011/0095069 A1 | 4/2011 | Patel et al. | |
| 2011/0095070 A1 | 4/2011 | Patel et al. | |
| 2011/0101065 A1 | 5/2011 | Milliman | |
| 2011/0114697 A1 | 5/2011 | Baxter, III et al. | |
| 2011/0114698 A1 | 5/2011 | Baxter, III et al. | |
| 2011/0114699 A1 | 5/2011 | Baxter, III et al. | |
| 2011/0114700 A1 | 5/2011 | Baxter, III et al. | |
| 2011/0114701 A1 | 5/2011 | Hessler | |
| 2011/0118761 A1 | 5/2011 | Baxter, III et al. | |
| 2011/0130788 A1 | 6/2011 | Orban, III et al. | |
| 2011/0139852 A1 | 6/2011 | Zingman | |
| 2011/0139853 A1 | 6/2011 | Viola | |
| 2011/0144640 A1 | 6/2011 | Heinrich et al. | |
| 2011/0147432 A1 | 6/2011 | Heinrich et al. | |
| 2011/0147434 A1 | 6/2011 | Hueil et al. | |
| 2011/0147435 A1 | 6/2011 | Heinrich et al. | |
| 2011/0192882 A1 | 8/2011 | Hess et al. | |
| 2011/0210156 A1 | 9/2011 | Smith et al. | |
| 2011/0220703 A1 | 9/2011 | Orban, III | |
| 2011/0248067 A1 | 10/2011 | Takei | |
| 2014/0008413 A1 * | 1/2014 | Williams | A61B 17/1155 227/179.1 |
| 2014/0367444 A1 | 12/2014 | Williams | |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2614784 A2 | 7/2013 |
| EP | 2682061 A2 | 1/2014 |
| EP | 2813188 A2 | 12/2014 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

OTHER PUBLICATIONS

AU Examination Report dated May 18, 2018, in AU Appln. No. 2014210642.

European Search Report EP14184195.7-1654 dated Mar. 17, 2015.

European Search Report dated Dec. 12, 2016, issued in EP Application No. 16174842.

\* cited by examiner

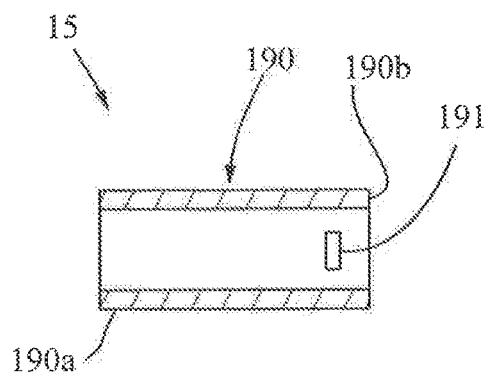
FIG. 16A
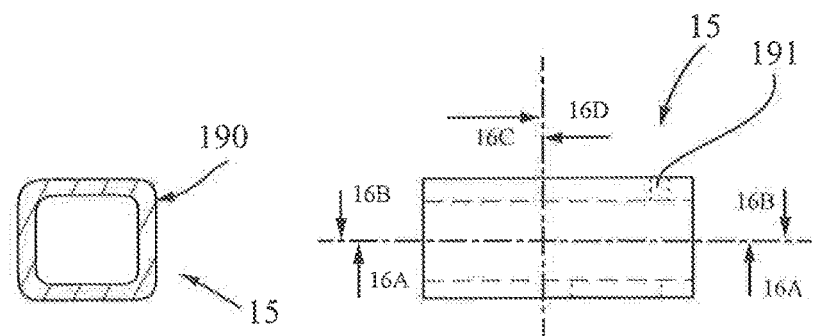
FIG. 16D
FIG. 16
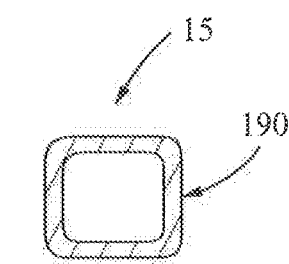
FIG. 16C
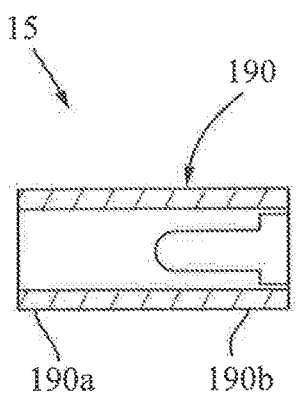
FIG. 16B

ANVIL ASSEMBLY WITH SLIDING SLEEVE

CROSS-REFERENCE TO RELATED APPLICATIONS

This application is a continuation of U.S. patent application Ser. No. 14/023,694 filed Sep. 11, 2013, the disclosure of the above-identified application is hereby incorporated by reference in its entirety.

BACKGROUND

Technical Field

The present disclosure relates generally to an anvil assembly which is suitable for use with a circular anastomosis stapler. More specifically, the present disclosure relates to an anvil assembly having a tiltable head with a sliding sleeve.

Background of Related Art

Circular anastomosis staplers which include an anvil assembly having a tiltable anvil head are known in the art. One such circular anastomosis stapler is disclosed in commonly owned U.S. Patent Application Publication No. 2008/0230581 ("'581 Publication") which is incorporated herein by reference in its entirety. The anvil assembly includes an anvil head pivotally secured on a distal end of a connection post of the anvil assembly. The anvil assembly is provided to a clinician in an operable position, i.e., with the anvil head perpendicular to the connection post.

During an anastomosis procedure, a purse string suture may be used to attach first and/or second sections of the tissue being joined together about the connection post of the anvil assembly. Following the firing operation of the circular anastomosis stapler and as the anvil head is separated from the cartridge assembly of the circular stapler, the anvil head pivots about the distal end of the connection post, to reduce the profile of the anvil head. The anvil assembly may be spring loaded to automatically tilt the anvil head to a maximum angle allowed by the circular stapler and/or anvil head geometry. Tilting the anvil head to reduce the profile of the anvil head within a vessel minimizes contact between the anvil head and the inner walls of the vessel to facilitate removal of the anvil head through an anastomosis ring, i.e., the annular stapled section of tissue, formed by the stapler.

In certain instances, an anastomosis donut, i.e., the tissue severed by an annular knife of the stapling assembly during an anastomosis procedure and the purse string suture(s), if used to secure the tissue section(s) about the anvil assembly, and/or other tissue or obstruction may become pinched by the anvil head as the anvil head is pivoted. When this occurs, the anvil head is inhibited from fully tilting. As a result, the anvil head may contact the interior of the vessel to a greater extent than necessary during withdrawal of the anvil head through the anastomosis ring. Contact of the interior of the vessel may cause unwanted tissue damage (i.e., damage to the anastomosis ring) and/or may result in higher retraction forces being necessary during removal of the anvil head through the vessel.

Therefore, it would be beneficial to have an anvil assembly including a sleeve configured to reposition the anastomosis donut to prevent pinching of the anastomosis donut by the tiltable anvil head, and, thus, allow complete tilting of the anvil head.

SUMMARY

Accordingly, an improved anvil assembly is provided. The anvil assembly includes an anvil center rod, a head assembly pivotally secured to the anvil center rod assembly from an operative position to a tilted position, and a sleeve slidably disposed about the anvil center rod. The sleeve is associated with the head assembly such that movement of the head assembly from the operative position towards the tilted position effects proximal movement of the sleeve about the anvil center rod.

In some embodiments, the sleeve assembly includes a sleeve body disposed about the anvil center rod assembly and a distally extending flange pivotally connected to the head assembly. A living hinge may be formed between the flange and the sleeve body. The head assembly may include a pivotal cam latch member and the flange is pivotally connected to the cam latch member.

In embodiments, the head assembly may include a housing, a post, a backup plate, and a cam latch member. The backup plate may be positioned to prevent pivotal movement of the head assembly from the non-tilted position to the tilted position prior to firing of a surgical stapling device. The backup plate may be movable to a second position to permit pivotal movement of the head assembly in relation to the anvil center rod assembly from the non-tilted position to the tilted position. The anvil head assembly may include a post which is pivotally secured to the anvil center rod, the sleeve member is operably engaged to the post. The sleeve member may be operably positioned to be engaged by the anvil assembly as the anvil assembly is pivoted from the operative position to the tilted position.

BRIEF DESCRIPTION OF THE DRAWINGS

Various embodiments of the presently disclosed tilt anvil assembly are disclosed herein with reference to the drawings wherein:

FIG. 16 is a side view of a slide member of the anvil assembly shown in FIGS. 14 and 15;

FIG. 16A is a cross-sectional bottom view taken along line 16A-16A shown in FIG. 16;

FIG. 16B is a cross-sectional top view taken along line 16B-16B shown in FIG. 16;

FIG. 16C is a cross-sectional end view taken along line 16C-16C shown in FIG. 16;

FIG. 16D is a cross-sectional end view taken along line 16D-16D shown in FIG. 16;

DETAILED DESCRIPTION OF EMBODIMENTS

Figure 1:
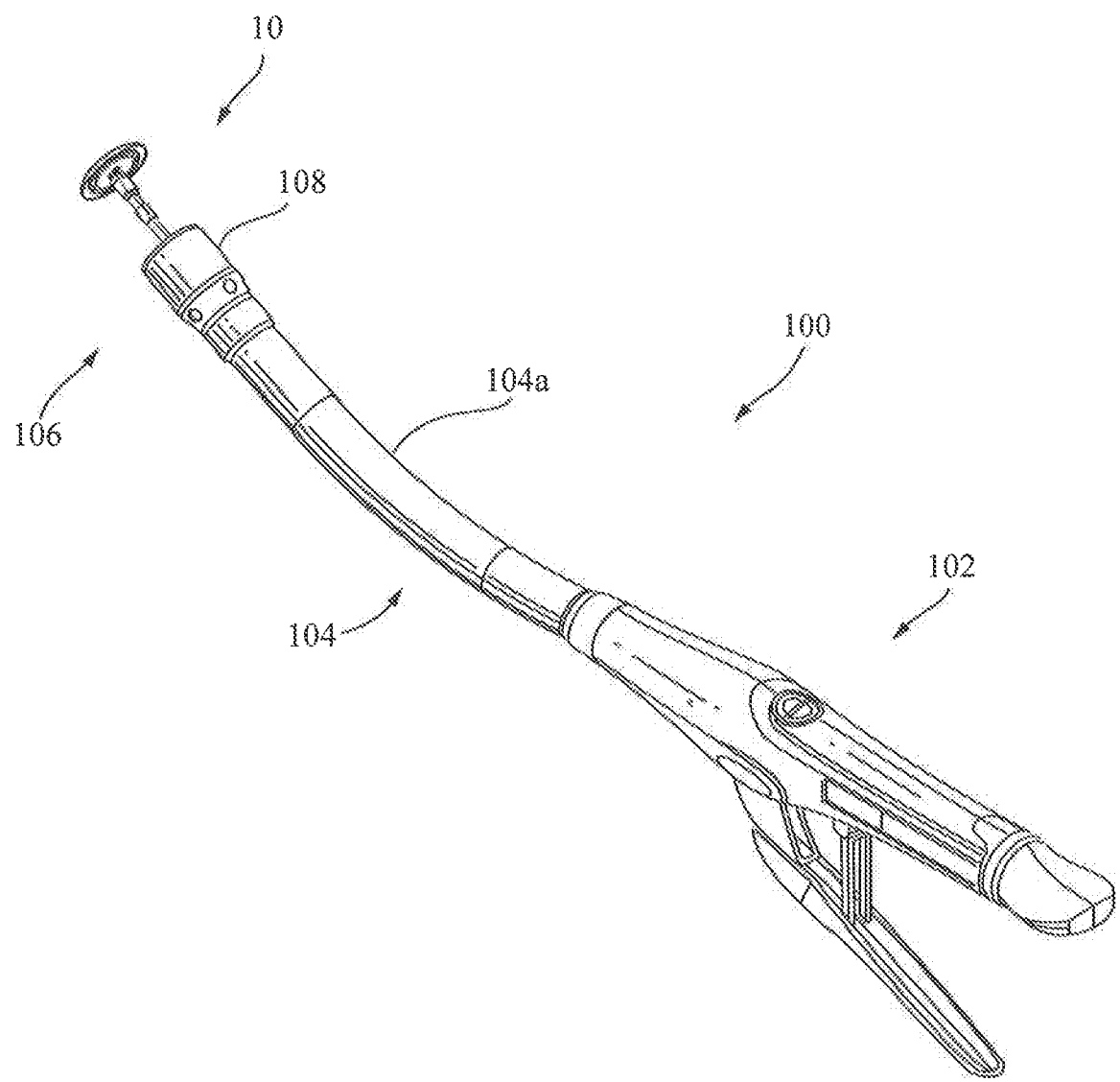
FIG. 1 is a side perspective view of a surgical stapling device including an anvil assembly according to an embodiment of the present disclosure.
Figure 2:
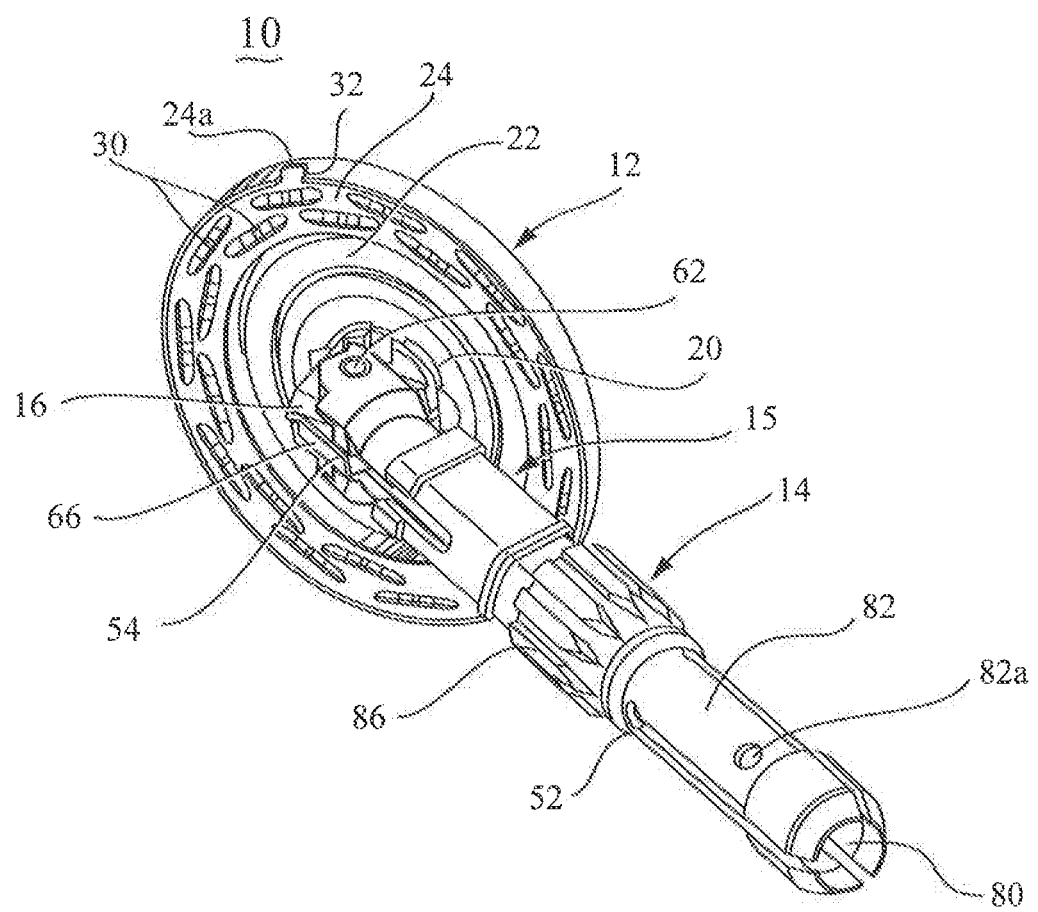
FIG. 2 is a side perspective view of the anvil assembly shown in FIG. 1, with the head assembly in a second or tilted position subsequent to firing of the surgical stapling device.

Embodiments of the presently disclosed anvil assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

FIGS. 1-13 illustrate a tiltable anvil assembly 10 which is suitable for use with a surgical stapling device 100 for performing surgical procedures, such as, for example, circular anastomoses of hollow tissue organs and hemorrhoid surgeries. With initial reference to FIG. 1, surgical stapling device 100 includes a proximal handle assembly 102, an elongated central body portion 104 including a curved elongated outer tube 104a, and a distal head portion 106. Alternately, in some surgical procedures, e.g., the treatment of hemorrhoids, it is desirable to have a substantially straight, shortened, central body portion. The length, shape and/or the diameter of body portion 104 and distal head portion 106 may be varied to suit a particular surgical procedure. Detailed descriptions of surgical stapler 100 are disclosed in commonly owned U.S. Pat. Nos. 7,364,060 and 7,303,106 ("the '060 Patent" and "the '106 Patent"), the contents of each of which are incorporated herein by reference in their entirety.

Referring to FIGS. 2-5, anvil assembly 10 includes a head assembly 12, a center rod assembly 14, and a sleeve member 15. Sleeve member 15 is configured to reposition an anastomosis donut and/or other tissue or obstruction (not shown) about center rod assembly 14 following the firing of surgical stapling device 100 to allow head assembly 12 to pivot relative to center rod assembly 14 without pinching the anastomosis donut between head assembly 12 and center rod assembly 14 as described in further detail below. As described above, an anastomosis donut is the tissue severed from the anastomosis site by an annular knife of a circular stapling device during an anastomosis procedure using a circular stapling device.

In one embodiment, head assembly 12 includes a post 16, a housing 18, a backup member or plate 20, a cutting ring 22, a cutting ring cover 23, an anvil plate 24, a cam latch member 26, and a retainer member 27. As shown, post 16 is monolithically formed with and centrally positioned within head 18. Alternatively, post 16 and head 18 may be formed as separate components that are joined using, adhesives, welding or any other suitable method. As will be described in further detail below, post 16 includes a pair of nubs 16a (FIG. 8) configured to engage anvil center rod assembly 14 to prevent counter-clockwise rotation of head assembly 12 relative to anvil center rod assembly 14. Anvil plate 24 is supported in an outer annular recess 28 (FIG. 3) of housing 18 and includes a plurality of staple deforming pockets 30 for receiving; and deforming staples (not shown). At least one tab 24a extends radially outwardly from anvil plate 24 and is received within a cutout 32 formed in an outer rim of housing 18. Tab 24a and cutout 32 function to align or properly position anvil plate 24 within annular recess 28 of housing 18.

Figures 3, 4, 5:
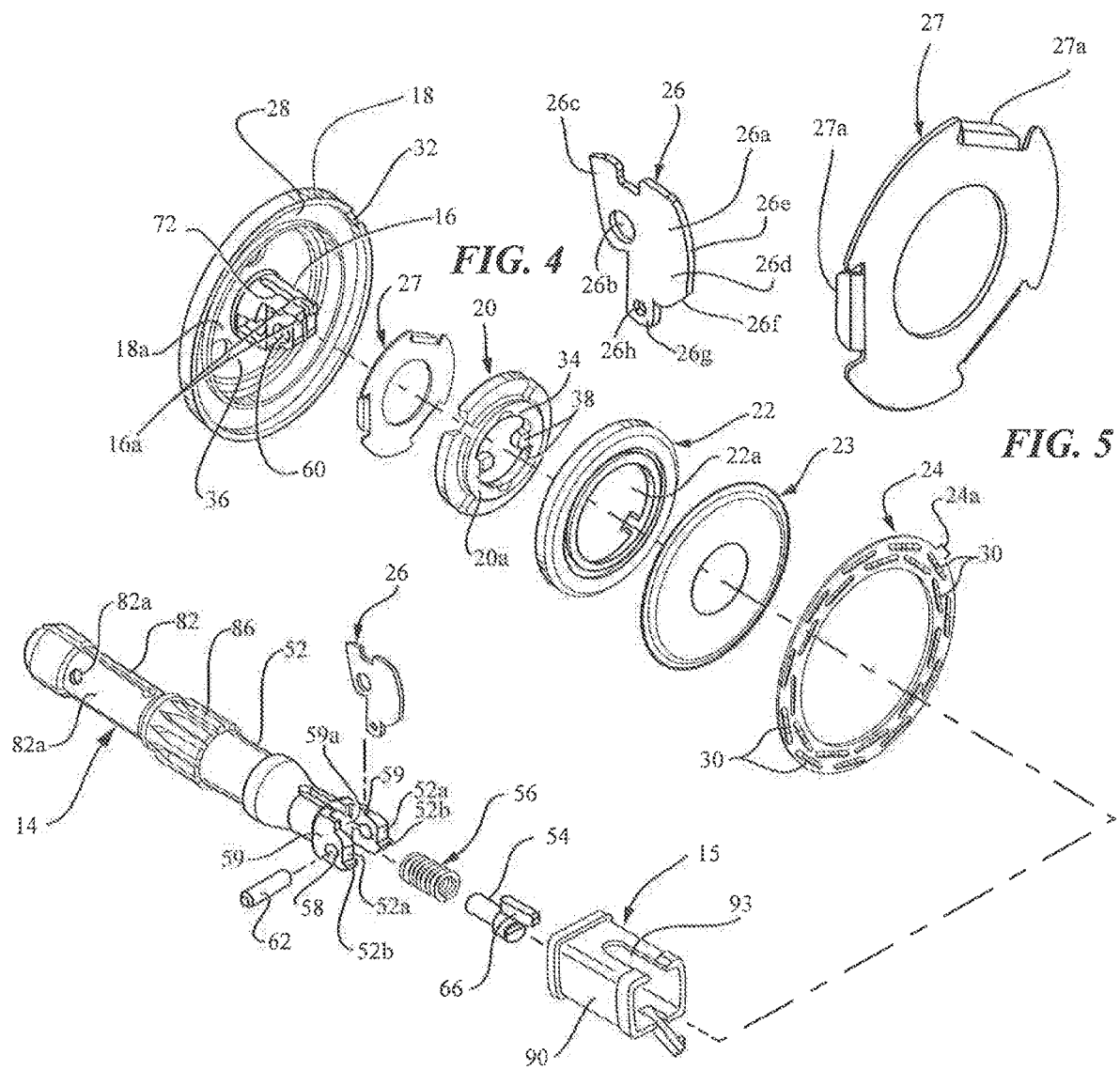
FIG. 3 is an exploded perspective view of the anvil assembly shown in FIG. 2.
FIG. 4 is an enlarged perspective view of a cam latch member of the anvil assembly shown in FIGS. 2 and 3.
FIG. 5 is an enlarged perspective view of a retainer member of the anvil assembly shown in FIGS. 2 and 3.

With particular reference to FIG. 3, backup plate 20 includes a central opening 34 which is positioned about post 16 within an inner annular recess 36 of housing 18 between post 16 and outer annular recess 28. Backup plate 20 includes a raised platform 20a. Cutting ring 22 includes an opening 22a having a configuration substantially the same as platform 20a. In one embodiment, cutting ring 22 is formed from polyethylene, or other suitable plastic, and is fixedly secured to backup plate 20 using, for example, an adhesive, to form a backup plate/cutting ring assembly. Backup plate 20 is formed from a hard material, e.g., a metal. Alternately other materials of construction may be used to construct backup plate 20 and cutting ring 22. Further, backup plate 20 and cutting ring 22, in the alternative, may be formed as a single or unitary structure.

A cutting ring cover 23 may be secured to an outwardly facing or proximal surface 40 of cutting ring 22 using, for example, an adhesive. Cutting ring 22 and backup plate 20 are slidably mounted about post 16. Backup plate 20 includes a pair of inwardly extending fingers 38 which will be described in further detail below. Retainer member 27 is positioned in inner annular recess 36 between backup plate 20 and a back wall 18a of housing 18 and prevents backup plate 20 and cutting ring 22 from moving or being pushed into inner annular recess 36 of housing 18 until a predetermined force sufficient to deform tabs 27a has been applied to the backup plate/cutting ring assembly. The predetermined force may be close to but is less than the force applied by an annular cutting blade of a surgical stapling device when it engages, for example, the cutting ring of anvil assembly 10. When the predetermined force is reached, e.g., during cutting of tissue, backup plate 20 is urged into inner annular recess 36 and compresses tabs 27a of retainer member 27.

Anvil center rod assembly 14 includes a center rod 52, a plunger 54, and plunger spring 56. A first end of center rod 52 has a pair of arms 59 which define a cavity 59a. Each arm 59 has a transverse throughbore 58 which is aligned with a central longitudinal axis of center rod 52. Post 16 of anvil head assembly 12 is dimensioned to be positioned within cavity 59a and includes a transverse throughbore 60. A pivot member 62 pivotably secures post 16 to center rod 52 via throughbores 58 and 60 such that anvil head assembly 12 is pivotably mounted to anvil center rod assembly 14.

With particular reference to FIGS. 3 and 4, cam latch member 26 includes a body 26a having a throughbore 26b. Throughbore 26b is dimensioned to receive pivot member 62 such that cam latch member 26 is pivotally mounted within transverse slot 72 (FIG. 3) of post 16 about pivot member 62. As shown in FIG. 4, cam latch member 26 includes a first body portion 26c which extends partially from slot 72 (FIG. 3) of post 16 and is positioned to be engaged by finger 66 of plunger 54. Cam latch member 26 also includes an edge 26f which is urged into engagement with an inner periphery of backup plate 20 (FIG. 10) by finger 66 of plunger 54 when anvil head 12 is in the non-tilted or operative position. Cam latch member 26 further includes a connector portion 26g which defines a throughbore 26h dimensioned to receive a pivot member 94 (FIG. 6) of sleeve member 15 such that cam latch member 26 is pivotally secured to sleeve member 15. Alternatively, cam latch member 26 and sleeve member 15 may be connected by a pivot member (not shown) extending from connector portion 26g of cam latch member 26 into engagement with an opening (not shown) formed in sleeve member 15.

Figure 10:
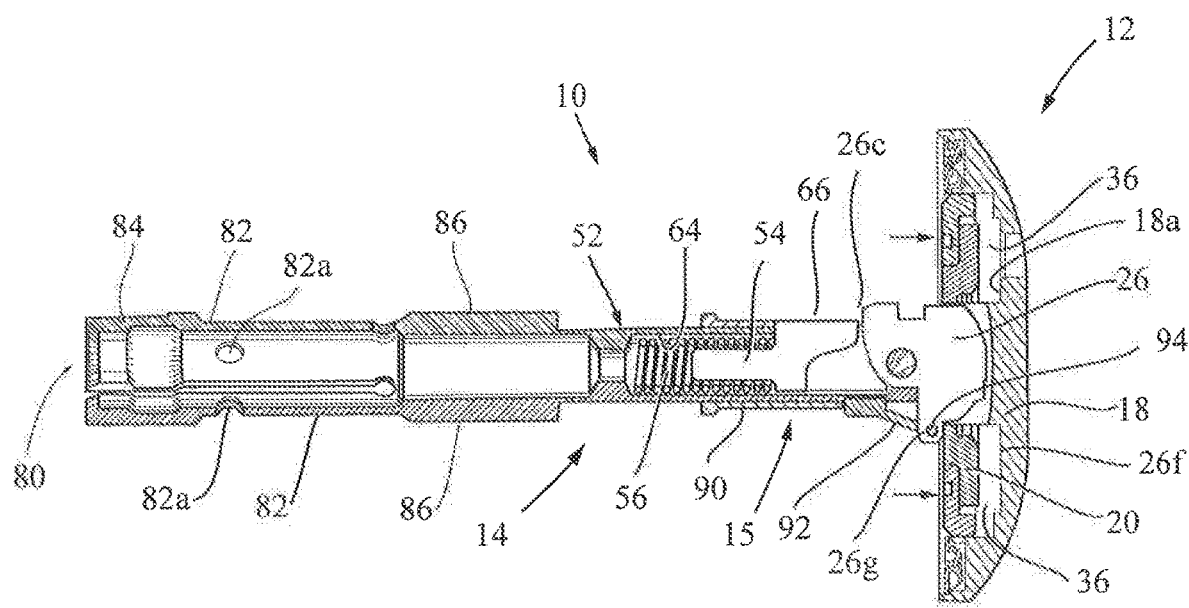
FIG. 10 is a cross-sectional side view of the anvil assembly shown in FIG. 9, in the first or operable position pre-firing.

Referring to FIG. 10, plunger 54 is slidably positioned in a bore 64 formed in the first end of center rod 52. Plunger 54 includes an engagement finger 66 which is offset from the pivot axis of anvil head assembly 12 and is biased into engagement with an edge 26c of cam latch member 26. As will be described in further detail below, engagement of finger 66 with edge 26c of cam latch member 26 presses edge 26f against an inner periphery of back plate 20 and post 16 to urge anvil head assembly 12 to the pivoted or tilted position (FIG. 12) on center rod 52. In the pre-fired position, fingers 38 formed on backup plate 20 are positioned adjacent top surface 52a and protrusions 52b of center rod 52 to prevent anvil head assembly 12 from pivoting about pivot member 62 (FIG. 7), When anvil assembly 10 is attached to surgical stapling device 100 (FIG. 1) and the device is fired in the manner described in the '106 Patent, backup plate 20 and cutting ring 22 are pushed into inner annular recess 36 of housing 18 about post 16, in the direction indicated by arrow "A" in FIG. 11, by a knife blade (not shown). When this occurs, fingers 38 move into annular recess 36 away from top surface 52a and protrusions 52b of center rod 52 to permit plunger 54 (FIG. 11) to pivot anvil head assembly 12 about pivot member 62. Retainer member 27 prevents inadvertent or premature movement of backup plate 20 into inner annular recess 36 to prevent premature or inadvertent tilting of anvil head assembly 12.

Referring now to FIGS. 3 and 10, a second end of center rod 52 includes a bore 80 defined by a plurality of flexible arms 82. Flexible arms 82 each include an opening 82a dimensioned to receive a projection formed on or connected to a removable trocar (not shown) or the like. The distal ends of each of flexible arms 82 include an internal shoulder 84 (FIG. 10) dimensioned to releasably engage an anvil retainer (not shown) of a surgical stapling device 100 (FIG. 1) to secure anvil assembly 10 to surgical stapling device 100. A plurality of splines 86 are formed about center rod 52. Splines 86 function to align anvil assembly 10 with the staple holding portion of surgical stapling device 100.

Figure 6A:
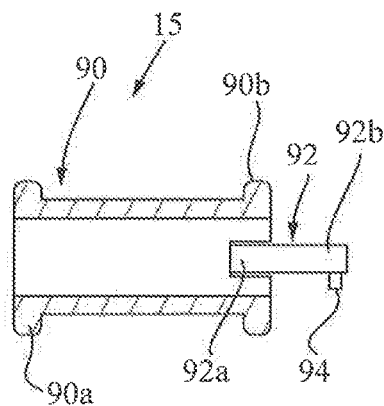
FIG. 6A is a cross-sectional bottom view taken along line 6A-6A shown in FIG. 6.
Figures 6, 6C, 6D:
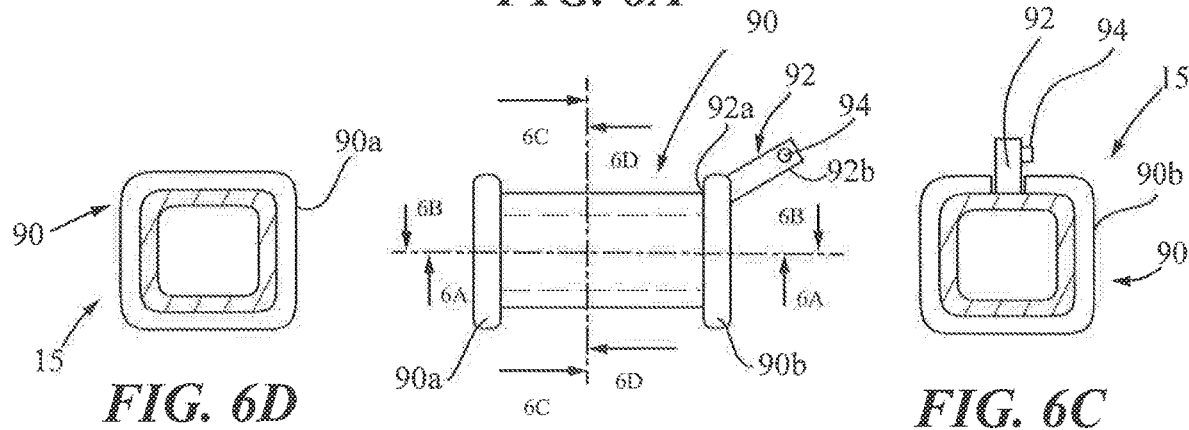
FIG. 6 is a side view of the sleeve member of the anvil assembly shown in FIG. 2-5.
FIG. 6C is a cross-sectional end view taken along line 6C-6C shown in FIG. 6.
FIG. 6D is a cross-sectional end view taken along line 6D-6D shown in FIG. 6.
Figure 6B:
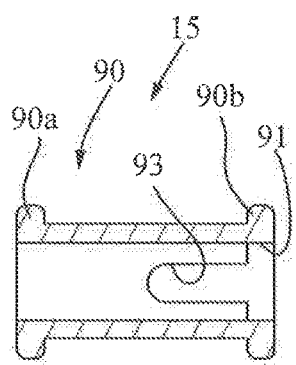
FIG. 6B is a cross-sectional top view taken along line 6B-6B shown in FIG. 6.

With particular reference now to FIGS. 6-6D, sleeve member 15 includes a sleeve body 90 and a flange 92 extending distally from sleeve body 90. Sleeve body 90 is substantially tubular and is configured to be received about a distal end of center rod 52 (FIG. 7) of center rod assembly 14 and to extend across the tissue gap defined between anvil plate 24 and a distal end of shell assembly 108 (FIG. 1). Sleeve body 90 is sized and dimensioned to slide proximally, as indicated by arrows "C" in FIG. 13, from a distal-most first position on center rod 52 when anvil assembly 10 is in the first or operable position (FIG. 9) to a proximal position on center rod 52 (FIG. 13) as head assembly 12 pivots relative to anvil center rod assembly 14.

Figure 9:
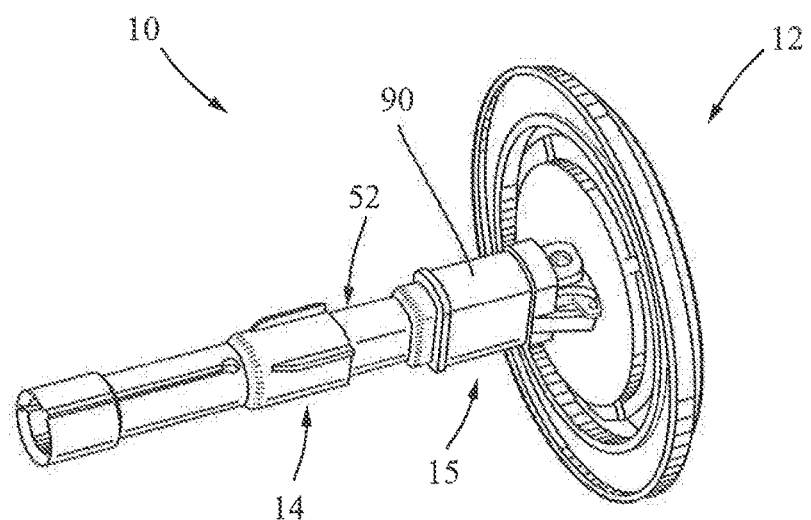
FIG. 9 is a perspective side view of the anvil assembly shown with the head assembly in a first or operable position.

Sleeve body 90 optionally includes annular lips 90a, 90b formed on proximal and distal ends, respectively. Annular lips 90a, 90b are configured to maintain the anastomosis donut and/or other tissue or obstruction (not shown) about sleeve body 90 as sleeve body 90 is moved proximally about center rod 52 during pivoting of head assembly 12 from the operable position to the tilted position. As described above, during an anastomosis procedure, the first and/or second sections of the tissue being joined (not shown) may be secured to anvil assembly 10 using a purse string suture(s) (not shown). The purse string suture(s) facilitate positioning and securing of the anastomosis donut about sleeve body 90. Sleeve body 90 defines notch 91 configured to accommodate post 16 and cam latch member 26 (FIG. 3) of head assembly 12 when sleeve body 90 is in the first, distal-most position (FIG. 9). Sleeve body 90 further defines a longitudinal slot 93 configured to accommodate finger 66 of plunger 54 of anvil center rod assembly 14 when sleeve body 90 is in the first, distal-most position (FIG. 9).

Figure 12:
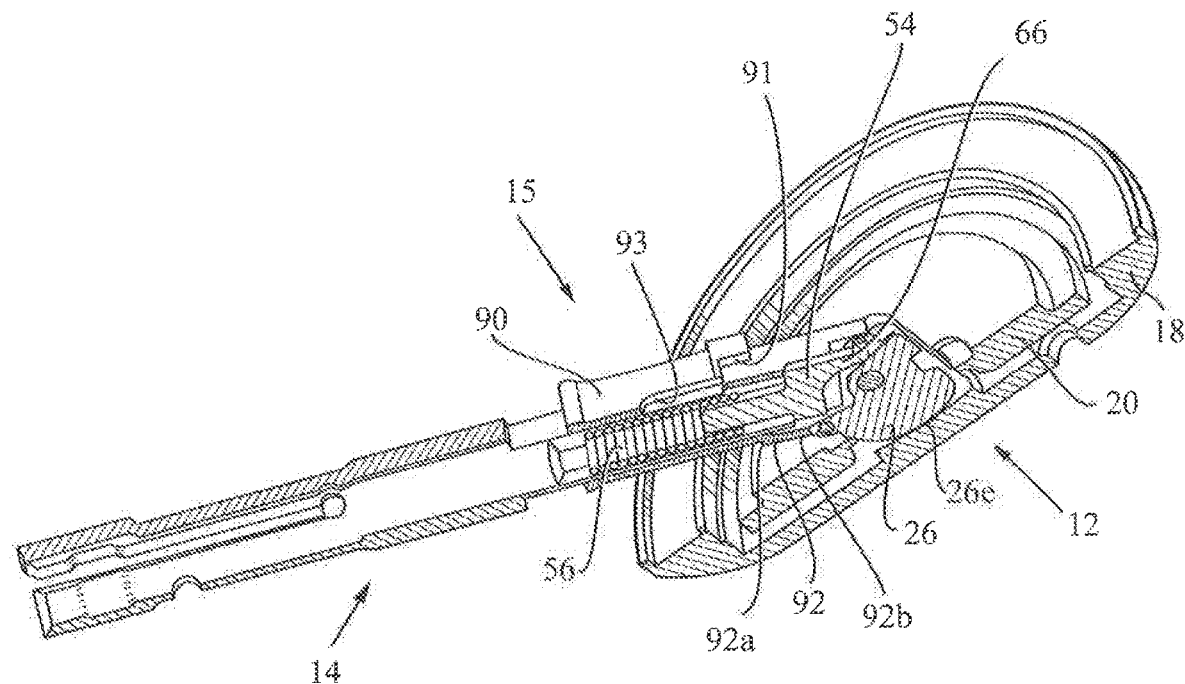
FIG. 12 is a cross-sectional perspective view of the anvil assembly shown in FIGS. 9-11, with the head assembly in the second or tilted position.

Flange 92 extends distally from sleeve body 90 and engages cam latch member 26 of head assembly 12. A first end 92a of flange 92 forms a living hinge with sleeve body 90 to permit flexing of flange 92 relative to sleeve body 90. A second end 92b of flange 92 is pivotally secured to connector portion 26g (FIG. 4) of cam latch member 26 of head assembly 12. As shown, flange 92 includes a pivot member 94 which is pivotally received within throughbore 26h formed in connector portion 26g of cam latch member 26. As noted above, in an alternative embodiment, cam latch member 26 may instead include a pivot member (not shown) configured for reception within an opening (not shown) defined by flange 92 of sleeve body 90. Flange 92 is slidably supported adjacent center rod 52 between sleeve member 15 and cam latch member 26 as cam latch member 26 is pivoted by finger 66 of plunger 54 during pivoting of head assembly 12 from the first position (FIG. 9) to the second position (FIG. 12). As cam latch member 26 pivots from the first position to the second position, the connection between connector portion 26g and flange 92 results in sleeve body 90 moving proximally, as indicated by arrows "C" in FIG. 13, from a distal-most position about center rod 52 to a proximal position. As described above, proximal movement of sleeve body 90 about center rod 52 relocates an anastomosis donut and/or other tissue or obstruction (not shown) formed during the anastomosis procedure to prevent pinching of the anastomosis donut, tissue and/or obstruction by head assembly 12 as head assembly 12 is pivoted to a tilted position (FIG. 12).

Figure 7:
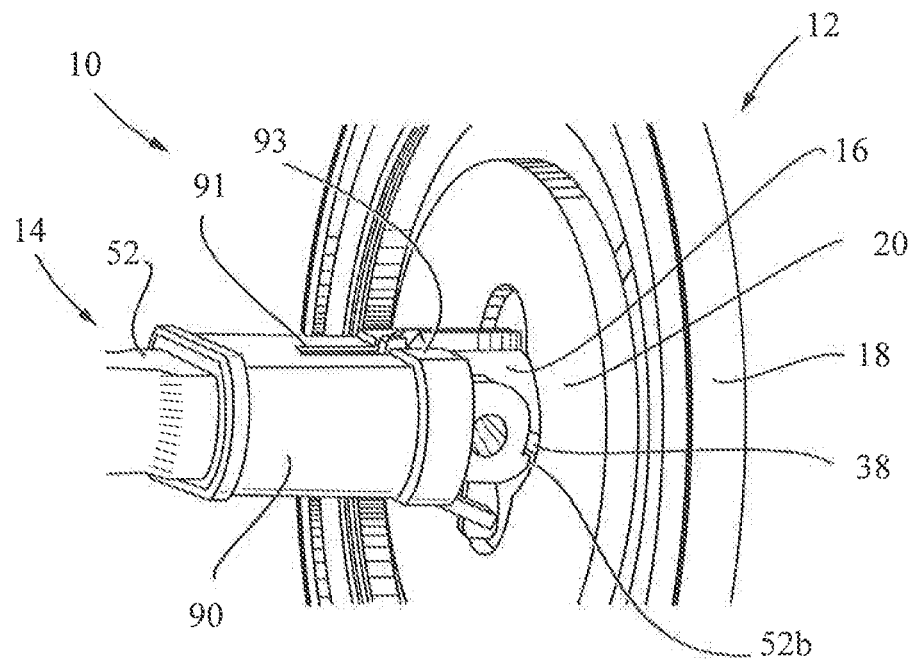
FIG. 7 is an enlarged side view of a portion of the anvil assembly shown in FIG. 2-5.
Figure 8:
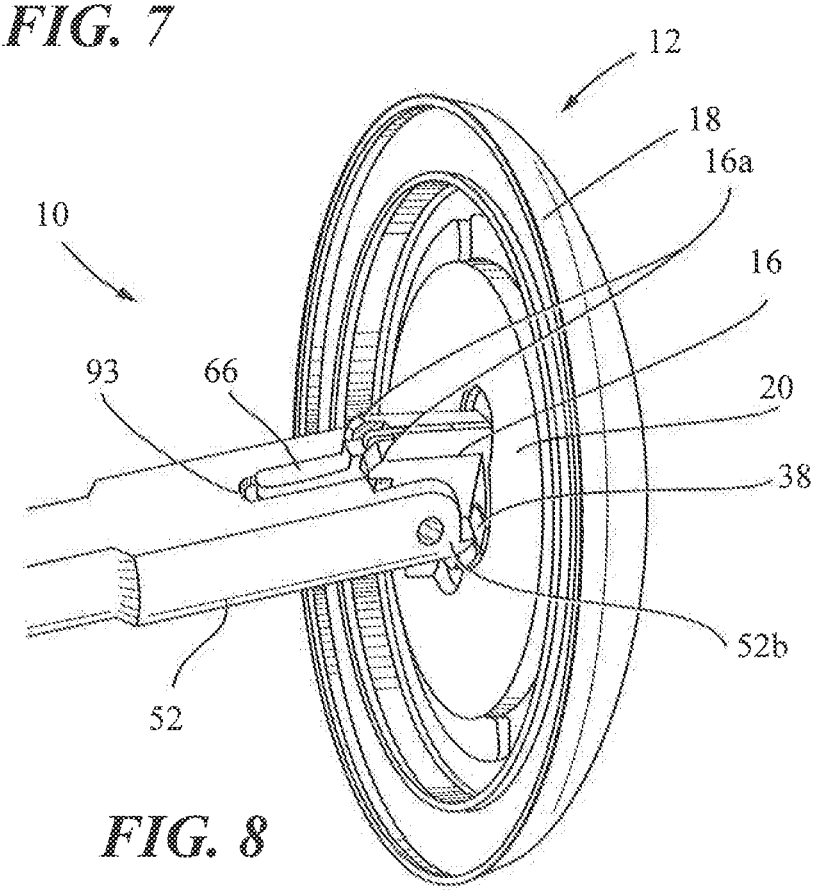
FIG. 8 is an enlarged side view of the portion of the anvil assembly shown in FIG. 7, with the sleeve member removed.

Referring to FIGS. 7 and 10, when anvil assembly 10 is in the prefired non-tilted position, backup plate 20 is spaced from back wall 18a of housing 18 by retainer 27 and fingers 38 of backup plate 20 are positioned adjacent top surface 52a and protrusion 52b of center rod 52 to prevent tilting of anvil head assembly 12 about pivot member 62. In the non-tilted position, sleeve body 90 covers the tilting mechanism, i.e., post 16 and cam latch member 26 of head assembly 12 and arms 59 of center rod 52 and pivot member 62, of tiltable anvil assembly 10.

Still referring to FIG. 10, finger 66 of plunger 54 is urged by spring 56 into engagement with body portion 26c of cam latch member 26 and post 16 to urge cam latch member 26 and head assembly 12 in a clockwise direction about pivot member 62 such that edge 26f of cam latch member 26 engages an inner periphery 20b of backup member 20 and anvil head assembly 12 move towards the tilted position (FIG. 12). The tilting of tiltable anvil assembly 10 facilitates insertion and/or removal of the anvil assembly to/from a hollow organ.

Figure 11:
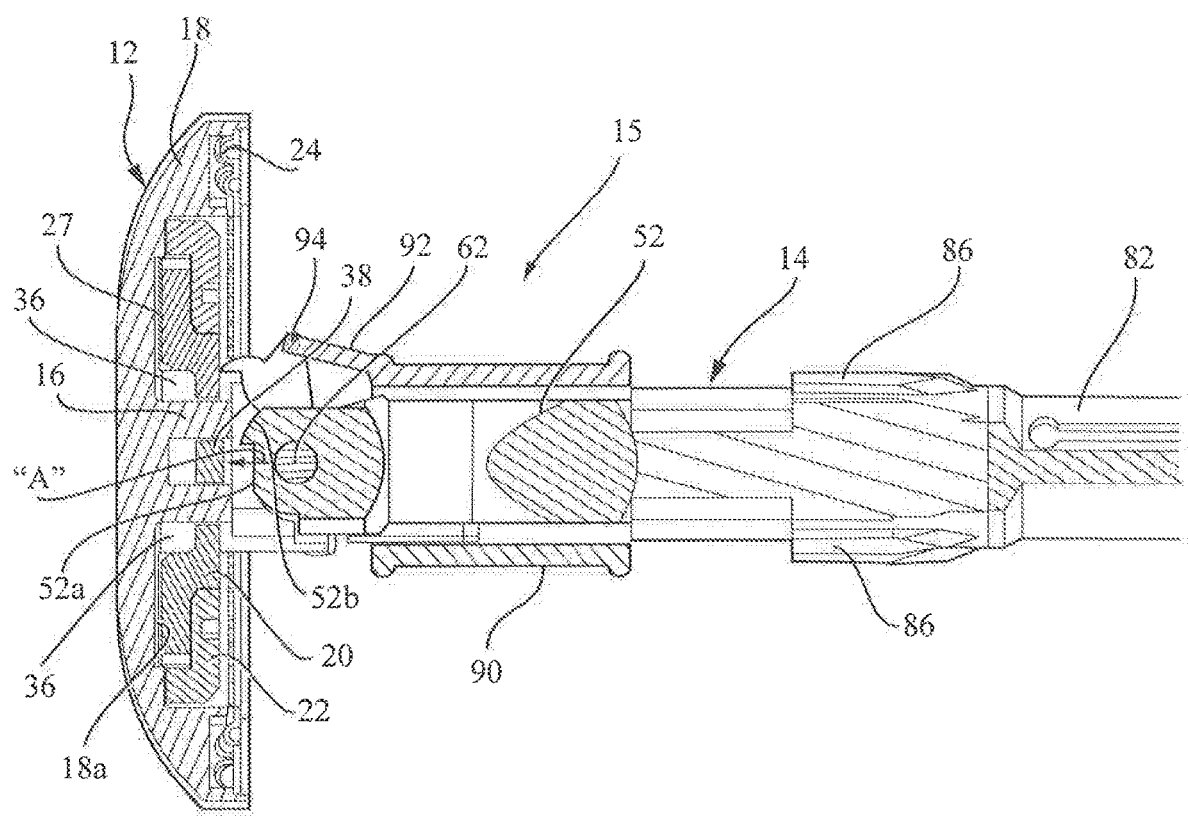
FIG. 11 is a cross-sectional side view of the anvil assembly shown in FIGS. 9 and 10, in the operable position subsequent to firing.

Referring to FIGS. 10 and 11, when anvil assembly 10 is attached to a stapling device 100 (FIG. 1) and the device is fired, a knife blade (not shown) of the stapling device engages cutting ring 22 to move cutting ring 22 (FIG. 3) and backup plate 20 in the direction indicated by arrow "A" in FIG. 11 into annular recess 36 of housing 18 of anvil head assembly 12. When this occurs, deformable tabs 27a (FIG. 3) of retainer 27 are deformed against back wall 18a of housing 18 and fingers 38 of backup member 20 move away from top surface 52a and protrusions 52b of center rod 52. Thereafter, engagement of plunger 54 with cam latch member 26 and subsequently with post 16 rotates cam latch member 36 and anvil head assembly 12 towards the tilted position (FIG. 12). It is noted that anvil head assembly 12 will not immediately tilt upon filing of stapling device 100 (FIG. 1) because, upon firing, anvil head assembly 12 is in an approximated position, i.e., the anvil head assembly 12 is in close alignment with shell assembly 108 (FIG. 1) of surgical stapling device 100 (FIG. 1). As such, the anvil head assembly 12 will begin to tilt as anvil head assembly 12 and shell assembly 108 of the stapling device 100 are unapproximated.

Figure 13:
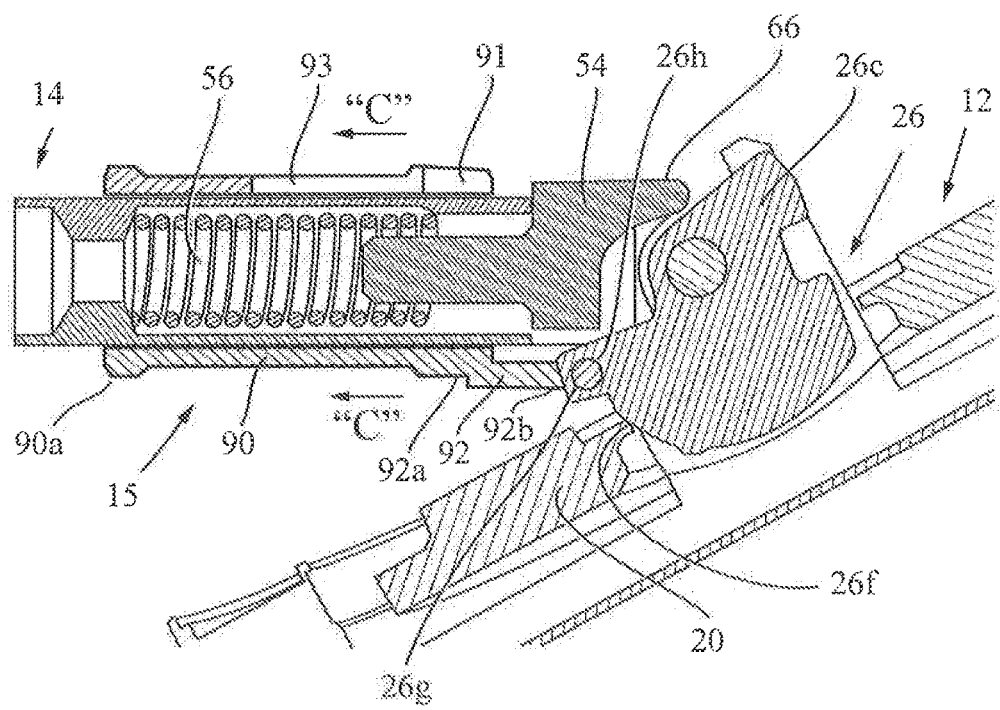
FIG. 13 is an enlarged cross-sectional side view of a portion of the anvil assembly shown in FIGS. 9-12.
Figure 14:
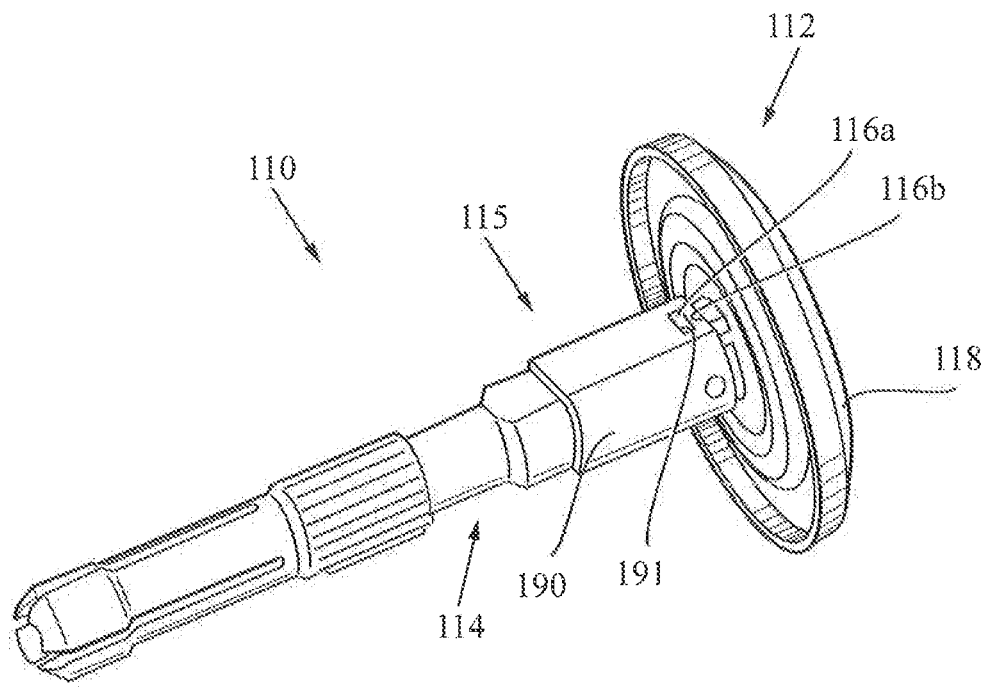
FIG. 14 is a perspective side view of an anvil assembly according to an alternative embodiment of the present disclosure, in a first or operable position.

Referring to FIGS. 12 and 13, as anvil head assembly 12 pivots towards its tilted position, finger 66 of plunger 54 maintains surface 26e of cam latch member 26 in contact with backup plate 20 to prevent backup plate 20 from sticking to the knife blade as the knife blade is retracted. It is noted that curved surface 26e of cam latch member is configured to eliminate any gap and ensure contact between surface 26e of cam latch member 26 and backup plate 20 to hold backup plate 20 in place during and after the knife blade is retracted such that the cutting ring and backup plate assembly stay in their correct position during tilting of anvil assembly 12.

As anvil head assembly 12 pivots towards the tilted position, pivotal engagement of flange 92 of sleeve member 15 with cam latch member 26 causes sleeve body 90 to slide proximally about center rod 52 of anvil center rod assembly 14. More particularly, the pivoting of cam latch member 26 applies a proximal force to sleeve body 90 through flange 92 to effect linear movement of sleeve body 90 about center rod 52. More specifically, the pivotal engagement between flange 92 and cam latch member 26 and the living hinge formed between flange 92 and sleeve body 90 allow flange 92 to flex to translate the pivoting motion of cam latch member 26 into a proximal linear motion of sleeve body 90. In this manner, the anastomosis donut and/or other tissue or obstruction (not shown) received about sleeve body 90 is moved proximally away from head assembly 12, to prevent pinching of the anastomosis donut and/or other tissue or obstruction between head assembly 12 and anvil center rod assembly 14. As described above, annular lips 90a, 90b formed on proximal and distal ends, respectively, of sleeve body 90 engage the anastomosis donut and/or other tissue or obstruction to facilitate movement of the donut/tissue/obstruction away from the tilting mechanism.

Although shown and described as being operably connected to cam latch member 26, it is envisioned that sleeve body 90 of sleeve member 15 may instead be operably connected to post 16 of head assembly 12 of anvil assembly 10. Furthermore, although shown as relates to anvil assembly 10, it is envisioned that the aspects of the present disclosure may be modified for use with any anvil assembly having an anvil head capable of being pivoted from a first, operable position, to a second, tilted position.

With reference now to FIGS. 14-18, an alternative embodiment of a tiltable anvil assembly according to the present disclosure is shown generally as anvil assembly 110. Anvil assembly 110 is substantially similar to anvil assembly 10 described hereinabove and will only be described as relates to the differences therebetween. Anvil assembly 110 includes a head assembly 112, an anvil center rod assembly 114, and a sleeve member 115.

Figure 15:
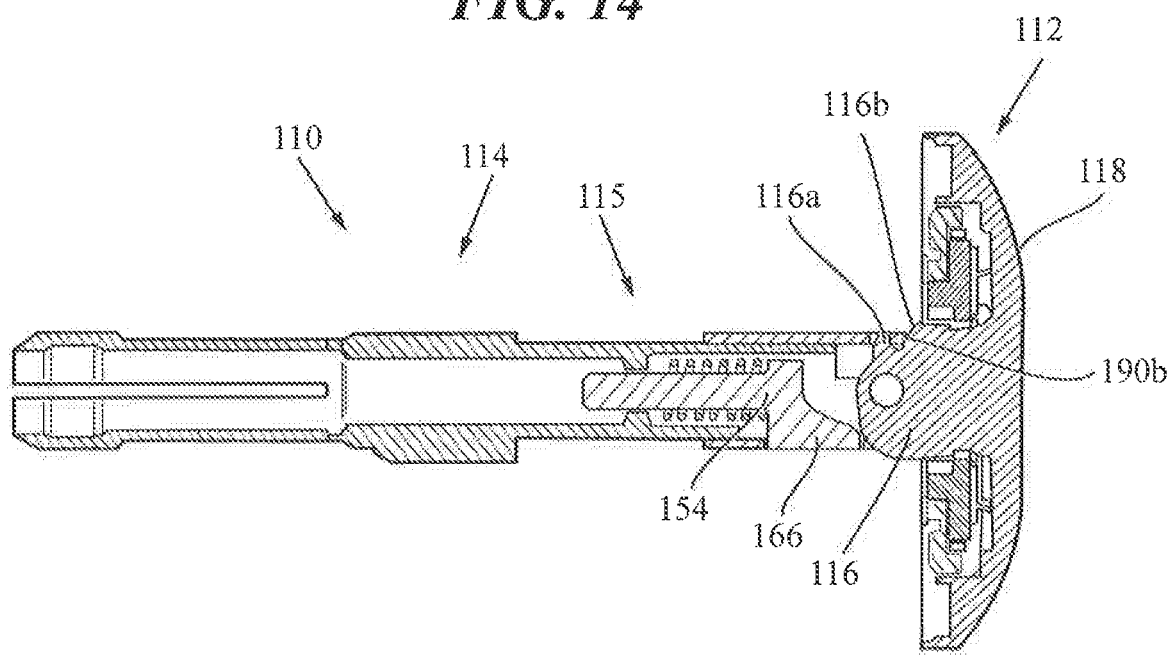
FIG. 15 is a cross-sectional side view of the anvil assembly shown in FIG. 14.

Head assembly 112 includes a housing 118 and a post 116. Post 116 includes a tab 116a and an engagement surface 116b. Tab 116a of post 116 is configured to be loosely received within an opening 191 formed in a sleeve body 190 of sleeve member 115 when anvil assembly 110 is in a first or operable position (the non-tilted position; see FIGS. 14 and 15). Engagement surface 116b of post 116 is configured to engage a distal end 190b of sleeve body 190 as head assembly 112 pivots relative to anvil center rod assembly 114. It is envisioned that post 116 may further include a cam surface for engagement by finger 166 of plunger 154 (FIG. 15).

Figure 17:
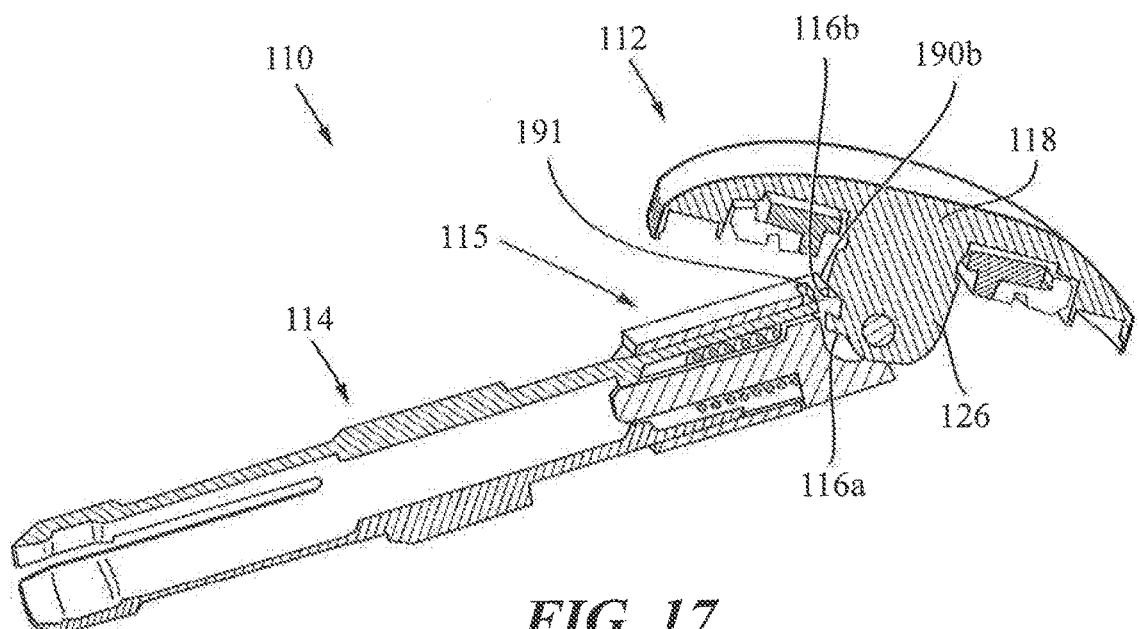
FIG. 17 is a cross-sectional perspective view of the anvil assembly shown in FIGS. 14 and 15, in a second or tilted position.
Figure 18:
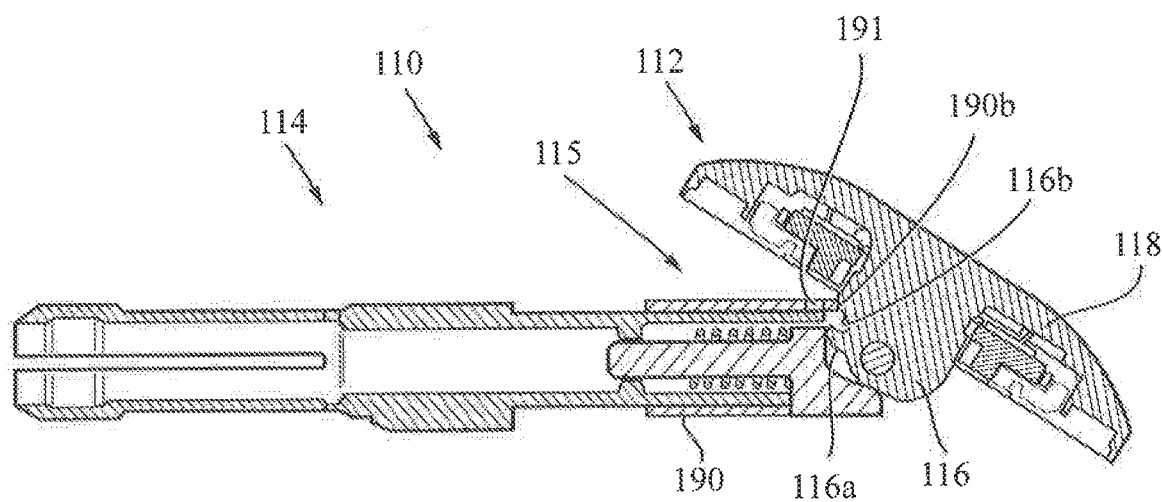
FIG. 18 is a cross-sectional side view of the anvil assembly shown in FIG. 17.

Sleeve member 115 includes sleeve body 190. Sleeve body 190 includes a substantially tubular member configured to be slidably received about a distal portion of anvil center rod assembly 114 in a sliding manner. Although not shown, sleeve member 115 may include a lip formed about one or both of proximal and distal ends 190a, 190b to facilitate retention of an anastomosis donut (not shown) about sleeve body 190. As noted above, sleeve body 190 defines an opening 191 adjacent a distal end configured to selectively receive tab 116a of post 116 of head assembly 112. As also noted above, a distal end 190b of sleeve body 190 is configured to be engaged by engagement portion 116b of post 116 of head assembly 112 during pivoting of head assembly 112 from the first or operable position (FIGS. 14 and 15) to a second or tilted position (FIGS. 17 and 18). It is envisioned that engagement portion 116b of post 116 may be shaped as a cam surface.

As described above with respect to anvil assembly 10, subsequent to firing of stapling device 100, head assembly 112 of anvil assembly 110 is configured to pivot relative to anvil center rod assembly 114. As head assembly 112 pivots to the second tilted position, tab 116a formed on post 116 of head assembly 112 is withdrawn from within opening 191 formed in sleeve body 190 of sleeve assembly 115. As tab 116a is withdrawn from opening 191, engagement surface 116b of post 116 engages distal end 190b of sleeve body 190. Engagement of sleeve body 190 by engagement surface 116b of post 116 moves sleeve body 190 in a proximal direction. In this manner, an anastomosis donut (not shown) received about sleeve body 190 is moved proximally away from head assembly 112, to prevent pinching of the anastomosis donut and/or other tissue or obstruction between head assembly 112 and anvil center rod assembly 114 as head assembly 112 is pivoted to the tilted position.

Figure 19:
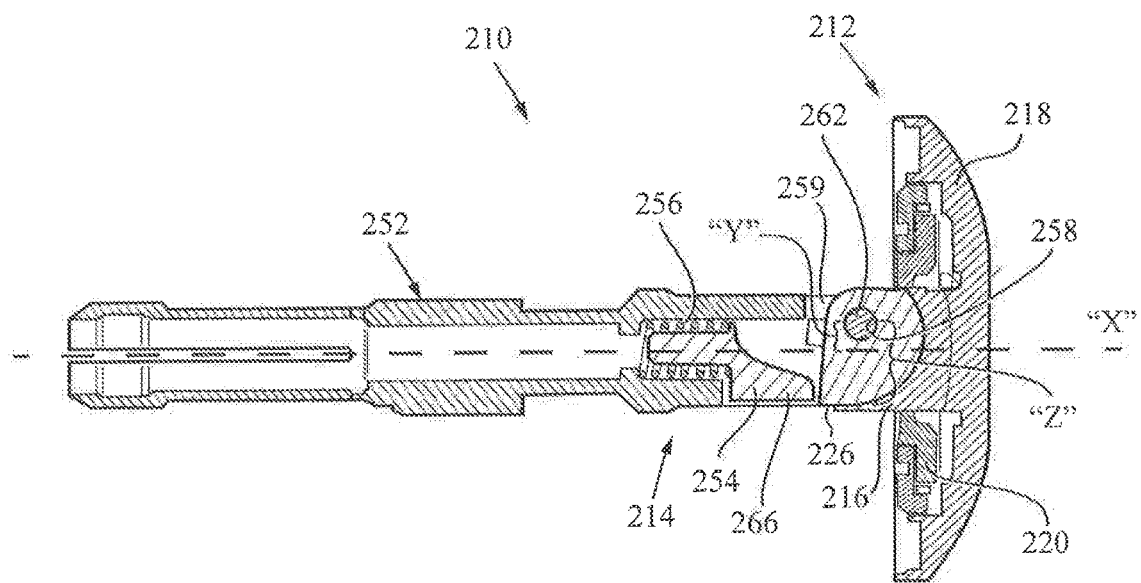
FIG. 19 is a cross-sectional side view an anvil assembly according to another embodiment of the present disclosure, in a first or operable position.
Figure 20:
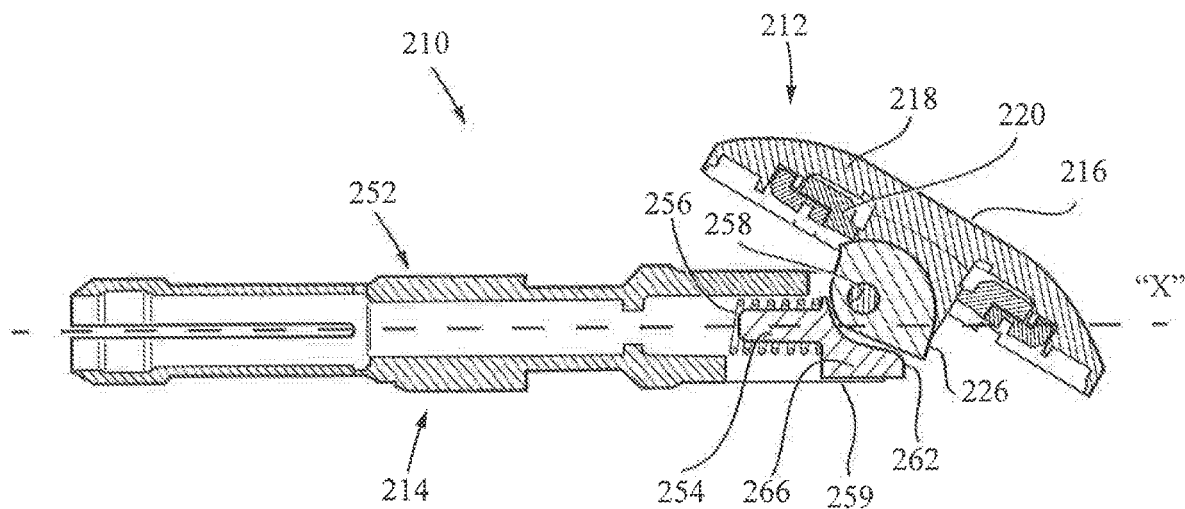
FIG. 20 is a cross-sectional side view of the anvil assembly shown in FIG. 19, in a second or tilted position.

With reference now to FIGS. 19 and 20, a tiltable anvil assembly according to another embodiment of the present disclosure is shown generally as anvil assembly 210. Anvil assembly 210 is substantially similar to anvil assemblies 10 and 110 described hereinabove, and therefore will only be described as relates to the differences therebetween. Anvil assembly 210 includes a head assembly 212 and an anvil center rod assembly 214. As will be described in further detail below, anvil assembly 210 may be modified for use with either of the above disclosed sleeve members 15 (FIG. 6), 115 (FIG. 16).

Head assembly 212 includes a housing 218, a post 216, and a cam latch member 226. Post 216 and cam latch member 226 may be integrally formed. Anvil center rod assembly 214 includes a center rod 252, a plunger 254, and plunger spring 256, Head assembly 212 is pivotally secured to center rod 252 by a pivot pin 262 which is received within a transverse throughbore (not shown) defined by post 216 and a pair of arms 259 of center rod 252. Cam latch member 226 defines a bore 258 which also receives pivot pin 262 to pivotally secure cam latch member 226 about pivot pin 262.

Transverse throughbore 258 is offset, i.e., laterally spaced, relative to a central longitudinal axis "x" of center rod 252, as indicated by reference character "y" in FIG. 19. By offsetting pivot pin 262 relative to central longitudinal axis "x", the distance between pivot pin 262 and a finger 266 of plunger 254, as indicated by reference character "z" in FIG. 19, is increased. Increasing the distance between pivot pin 262 and plunger 254 increases the tilting torque applied to head assembly 212 by plunger 254 without increasing the outer diameter of center rod 252. Increasing the tilting torque applied to head assembly 212 by plunger 254 increases the head tilting performance of anvil assembly 210. In particular, the offset arrangement of pivot pin 262 relative to longitudinal axis "x" permits the pivoting of head assembly 212 relative to anvil center rod assembly 214 when tissue or other obstruction disposed between head assembly 212 and anvil center rod assembly 214 might otherwise prevent head assembly 212 from pivoting relative to center rod assembly 214.

Anvil assembly 210 operates in a similar manner to anvil assemblies 10 and 110, described hereinabove. In particular, following actuation of surgical stapling device 100 (FIG. 1), engagement of a finger 266 of plunger 254 with cam latch member 226 rotates cam latch member 226 within housing 218 such that cam latch member 226 engages backup plate 220 to hold backup plate 220 in place as a knife blade (not shown) of surgical stapling device 10 (FIG. 1) is retracted. Finger 266 of plunger 254 also engages post 216 of head assembly 212 to cause pivoting of head assembly 212 relative to anvil center rod assembly 214 as head assembly 212 is moved away from shell assembly 108 (FIG. 1) of surgical stapling device 10 (FIG. 1).

In an alternative embodiment, an outer diameter of center rod 252 may be increased to accommodate a plunger (not shown) having a finger (not shown) that is spaced further from longitudinal axis "x" to increase the distance between pivot pin 262 and the finger of the plunger, thereby increasing the tilting torque applied by the finger to head assembly 212.

Any of the above disclosed embodiments may be modified for use with the surgical stapling instruments disclosed in commonly owned U.S. patent application Ser. No. 13/444,998 filed Apr. 12, 2012 and U.S. patent application Ser. No. 13/915, 953 filed Jun. 12, 2013, the contents of which are incorporated herein by reference in their entirety.

It will be understood that various modifications may be made to the embodiments disclosed herein. For example, the presently disclosed sleeve assemblies may be modified for use on an anvil assembly having a head assembly capable of one hundred and twenty degrees (120°) of tilt, i.e., capable of being pivoted in a counter-clockwise direction prior to firing to facilitate positioning of the anvil assembly within a lumen. Those skilled in the art will envision other modifications within the scope and spirit of the claims appended hereto.

What is claimed is:

1. An anvil assembly comprising:
an anvil center rod assembly;
a head assembly pivotally secured to the anvil center rod assembly and movable between an operative position and a tilted position, the head assembly including a housing and a post extending from the housing, the post including a tab; and
a sleeve positioned about the anvil center rod assembly and movable between a distal position and a proximal position, the sleeve defining an opening positioned to receive the tab when the head assembly is in the operative position and the sleeve is in the distal position, wherein receipt of the tab within the opening secures the sleeve in the distal position.

2. The anvil assembly of claim 1, wherein the sleeve includes a tubular body.

3. The anvil assembly of claim 1, wherein the tab is spaced from the opening when the head assembly is in the tilted position.

4. The anvil assembly of claim 1, wherein the head assembly further includes a backup plate, and a cam latch member.

5. The anvil assembly of claim 4, wherein the backup plate is positioned to prevent pivotal movement of the head assembly from the operative position to the tilted position prior to firing of a surgical stapling device.

6. The anvil assembly of claim 4, wherein the backup plate is movable to a tilted position to permit pivotal movement of the head assembly in relation to the anvil center rod assembly from the operative position to the tilted position.

7. The anvil assembly of claim 1, wherein the sleeve is positioned to be engaged by the head assembly as the head assembly is pivoted from the operative position to the tilted position to move the sleeve from the distal position to the proximal position.

8. The anvil assembly of claim 1, wherein the sleeve includes a first lip positioned about a proximal end of the sleeve and a second lip positioned about a distal end of the sleeve, the first and second lips being spaced from each other to receive and retain an anastomosis donut therebetween.

9. The anvil assembly of claim 1, wherein the anvil center rod assembly includes a plunger and the post includes a cam surface, the cam surface being engageable by the plunger.

10. An anvil assembly comprising:
an anvil center rod assembly;
a head assembly pivotally secured to the anvil center rod assembly and movable between an operative position and a tilted position, the head assembly including a housing and a post extending from the housing, the post including a tab; and
a sleeve positioned about the anvil center rod assembly and movable between a distal position and a proximal position, the sleeve defining an opening positioned to receive the tab when the head assembly is in the operative position, wherein the tab is spaced from the opening when the head assembly is in the tilted position, the sleeve including a first lip positioned about a proximal end of the sleeve and a second lip positioned about a distal end of the sleeve, the first and second lips being spaced from each other to receive and retain an anastomosis donut.

11. An anvil assembly comprising:
an anvil center rod assembly;
a head assembly pivotally secured to the anvil center rod assembly and movable between an operative position and a tilted position, the head assembly including a housing, a backup plate, a cam latch member, and a post extending from the housing, the post including a tab; and
a sleeve positioned about the anvil center rod assembly and movable between a distal position and a proximal position, the sleeve defining an opening positioned to receive the tab when the head assembly is in the operative position and the sleeve is in the distal position.

12. The anvil assembly of claim 11, wherein the sleeve includes a tubular body.

13. The anvil assembly of claim 11, wherein the tab is spaced from the opening when the head assembly is in the tilted position.

14. The anvil assembly of claim 11, wherein the backup plate is positioned to prevent pivotal movement of the head assembly from the operative position to the tilted position prior to firing of a surgical stapling device.

15. The anvil assembly of claim 11, wherein the backup plate is movable to a tilted position to permit pivotal movement of the head assembly in relation to the anvil center rod assembly from the operative position to the tilted position.

16. The anvil assembly of claim 11, wherein the sleeve is positioned to be engaged by the head assembly as the head assembly is pivoted from the operative position to the tilted position to move the sleeve from the distal position to the proximal position.

17. The anvil assembly of claim 11, wherein the sleeve includes a first lip positioned about a proximal end of the sleeve and a second lip positioned about a distal end of the sleeve, the first and second lips being spaced from each other to receive and retain an anastomosis donut therebetween.

18. The anvil assembly of claim 11, wherein the anvil center rod assembly includes a plunger and the post includes a cam surface, the cam surface being engageable by the plunger.

* * * * *